(12) United States Patent
Tripp et al.

(10) Patent No.: US 10,179,155 B2
(45) Date of Patent: Jan. 15, 2019

(54) PHOSPHODIESTERASE-4 INHIBITING PHYTOCHEMICAL COMPOSITIONS

(71) Applicant: Nature's Sunshine Products, Inc., Lehi, UT (US)

(72) Inventors: Matthew L. Tripp, Saratoga Springs, UT (US); Clinton J. Dahlberg, Saratoga Springs, UT (US); John G. Babish, Brooktondale, NY (US)

(73) Assignee: Nature's Sunshine Products, Inc., Lehi, UT (US)

( * ) Notice: Subject to any disclaimer, the term of this patent is extended or adjusted under 35 U.S.C. 154(b) by 3 days.

(21) Appl. No.: 15/122,387

(22) PCT Filed: Feb. 26, 2015

(86) PCT No.: PCT/US2015/017857
§ 371 (c)(1),
(2) Date: Aug. 29, 2016

(87) PCT Pub. No.: WO2015/130994
PCT Pub. Date: Sep. 3, 2015

(65) Prior Publication Data
US 2017/0065652 A1 Mar. 9, 2017

Related U.S. Application Data

(60) Provisional application No. 61/966,704, filed on Feb. 28, 2014.

(51) Int. Cl.
| | | |
|---|---|---|
| A61K 36/00 | (2006.01) | |
| A61K 36/185 | (2006.01) | |
| A61K 31/198 | (2006.01) | |
| A61K 31/51 | (2006.01) | |
| A61K 31/555 | (2006.01) | |
| A61K 31/717 | (2006.01) | |
| A61K 33/06 | (2006.01) | |
| A61K 9/00 | (2006.01) | |

(52) U.S. Cl.
CPC .......... *A61K 36/185* (2013.01); *A61K 9/0053* (2013.01); *A61K 31/198* (2013.01); *A61K 31/51* (2013.01); *A61K 31/555* (2013.01); *A61K 31/717* (2013.01); *A61K 33/06* (2013.01)

(58) Field of Classification Search
CPC ..................................................... A61K 36/00
See application file for complete search history.

(56) References Cited

U.S. PATENT DOCUMENTS

| | | |
|---|---|---|
| 6,288,104 B1 | 9/2001 | Gericke et al. |
| 8,372,414 B2 | 2/2013 | Crain et al. |
| 8,552,051 B2 | 10/2013 | Harvey et al. |
| 2009/0239884 A1* | 9/2009 | Epstein ............... A61K 31/519 514/262.1 |
| 2012/0004275 A1 | 1/2012 | Gericke et al. |

FOREIGN PATENT DOCUMENTS

| | | |
|---|---|---|
| WO | WO 2008/006082 A2 | 1/2008 |
| WO | WO 2013/116226 A2 | 8/2013 |

OTHER PUBLICATIONS

Anwar et al, "Cardiovascular and Other Pharmacological Approaches of Phosphodiesterase Enzyme Inhibitors." International Journal of Advances in Pharmacy Medicine and Bioallied Sciences; Biomedjournal; 2013; vol. 1; pp. 35-39.
Harvey et al, "Pharmacological Actions of the South African Medicinal and Functional Food Plant Sceletium Tortuosum and its Principal Alkaloids." Journal of Ethnopharmacology; Elsevier; Oct. 11, 2011; vol. 137, Issue 3; pp. 1124-1129.
Kimura et al, "L-Theanine Reduces Psychological and Physiological Stress Responses." Biological Psychology; Elsevier; Jan. 2007; vol. 74, Issue 1; pp. 39-45.
PCT Application No. PCT/US2015/017857; Filing Date Feb. 26, 2015; Matthew L. Tripp, International Search Report, dated May 22, 2015; 16 Pages.
PCT Application No. PCT/US2015/017858; Filing Date Feb. 26, 2015; Matthew L. Tripp, International Search Report, dated May 20, 2015; 12 Pages.

\* cited by examiner

*Primary Examiner* — Qiuwen Mi
(74) *Attorney, Agent, or Firm* — Thorpe North & Western, LLP; David W. Osborne

(57) ABSTRACT

Phosphodiesterase-4 (PDE4) inhibiting compositions comprising a *Sceletium* and an activity enhancer are disclosed and described. Methods and systems for inhibiting PDE4, as well as, dosage forms comprising a *Sceletium* extract and an activity enhancer are also disclosed. Additionally disclosed are methods for enhancing the potency or PDE4 inhibitory activity of a *Sceletium* extract by addition of an activity enhancer.

14 Claims, 1 Drawing Sheet

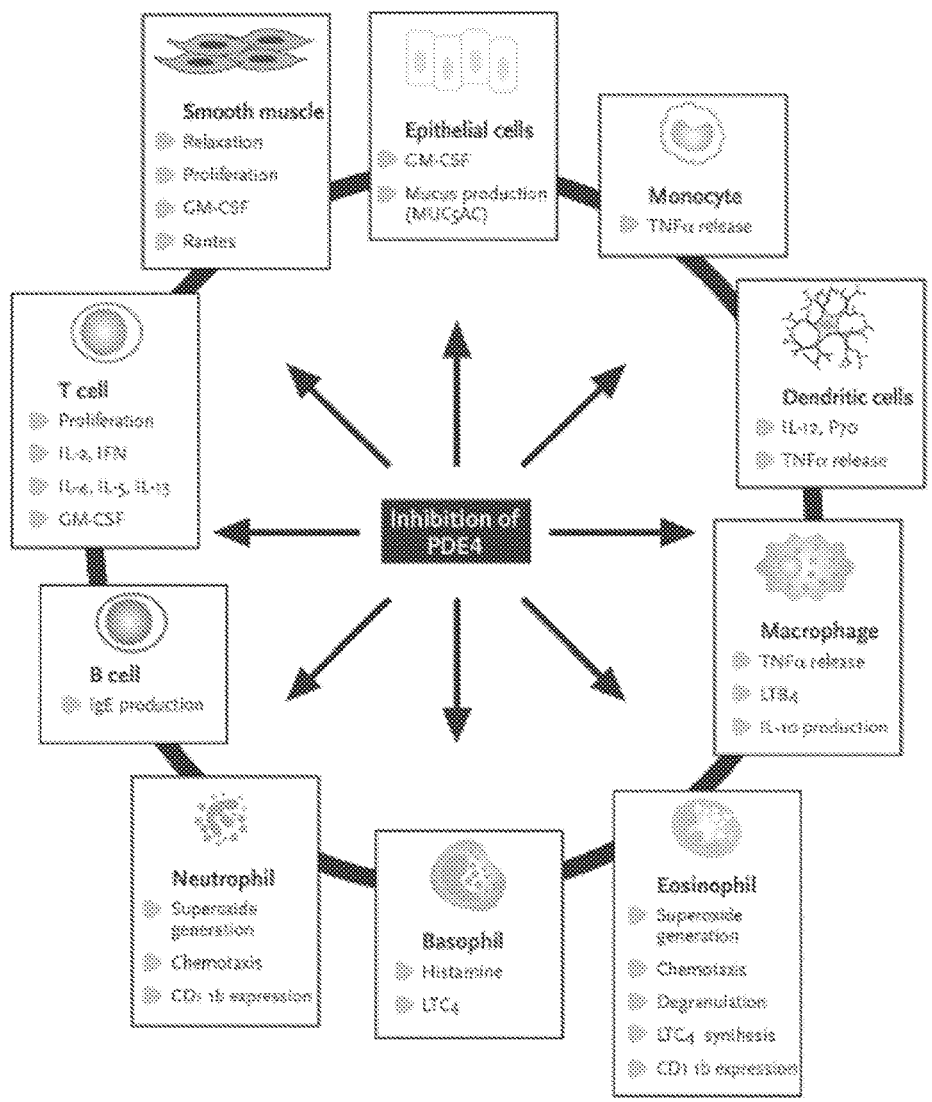

PHOSPHODIESTERASE-4 INHIBITING PHYTOCHEMICAL COMPOSITIONS

PRIORITY DATA

This application claims priority benefit to United States Provisional Patent Application Ser. No. 61/966,704 filed on Feb. 28, 2014 which is incorporated herein by reference. This application also incorporates by reference Patent Cooperation Treaty application serial no. PCT/US2015/017858 filed on Feb. 26, 2015 under Thorpe North & Western attorney docket no. 3901-003.PCT.

BACKGROUND

Phosphodiesterase type 4 (PDE4) is an enzyme that degrades the phosphodiester bond in the second messenger molecules of cellular cyclic adenosine monophosphate (cAMP), thereby regulating the localization, duration, and amplitude of cAMP signaling. cAMP binds to protein kinases enabling catalytic units of the protein kinases to phosphorylate substrate proteins. cAMP functions in several biochemical processes. The specific effect of cAMP depends on the protein kinase acted upon and the cell type. Sustaining cellular cAMP levels can inhibit numerous diseases and conditions. PDE4 inhibitors block the PDE4 induced degradation of cAMP thereby sustaining cellular cAMP levels and prolonging the effects of cAMP mediated physiological processes. Accordingly, PDE4 inhibitors can be valuable agents in treating or managing a number of related diseases or conditions.

Unfortunately, several PDE4 inhibiting compounds have narrow therapeutic windows and often cause undesirable side effects (i.e. nausea, diarrhea and headaches) when administered at therapeutically effective doses. Additionally, consumers continue to demand pharmaceuticals and nutraceuticals that include naturally derived active ingredients. Accordingly, the present inventors recognize a need for naturally derived PDE4 inhibitors which attain a desired level of PDE4 inhibition with little to no adverse side effects.

BRIEF DESCRIPTION OF THE FIGURES

Features and advantages of the invention will be apparent from the detailed description that follows, and which taken in conjunction with the accompanying FIGURE, together illustrate features of the invention. It is understood that this drawing merely depicts exemplary effects of PDE inhibition and is not, therefore, to be considered limiting of its scope.

FIG. 1 shows a schematic diagram of various tissue responses resulting from inhibition of PDE4.

DETAILED DESCRIPTION

Reference will now be made to exemplary invention embodiments and specific language will be used herein to describe the same. It will nevertheless be understood that no limitation in scope is thereby intended. Alterations and further modifications of inventive features described herein, and additional applications of inventive principles which would occur to one skilled in the relevant art having possession of this disclosure, are to be considered as inventive subject matter. Further, before particular embodiments are disclosed and described, it is to be understood that this disclosure is not limited to the particular process and materials disclosed herein as such may vary to some degree. It is also to be understood that the terminology used herein is used for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "an activity enhancer" includes one or more of such enhancers.

As used herein, the term "about" refers to a degree of deviation based on experimental error typical for the particular property identified. The latitude provided the term "about" will depend on the specific context and particular property and can be readily discerned by those skilled in the art. When used in connection with a numerical value, the term "about" is used to provide flexibility and allow the given value to be "a little above" or "a little below" the specific number stated. Further, unless otherwise stated, the term "about" shall expressly include "exactly," consistent with the discussion below regarding ranges and numerical data.

As used herein, a "subject" refers to an organism that produces PDE4 in the course of its cellular function. In one aspect, a subject can be a mammal. In another aspect, a subject can be a human. In another aspect, the subject can be of either male or female gender.

As used herein, "activity enhancer" refers to any agent or combination of agents that increases PDE4 inhibition when combined with *Sceletium*, or a *sceletium* extract as compared to the *Sceletium* or *sceletium* extract alone. In some embodiments, the amount of increase can exceed the additive effect that would be achieved by the *Sceletium* or *sceletium* extract and the activity enhancer individually. This synergistic (i.e. more than additive) effect can occur when both the *Sceletium* or *sceletium* extract and the activity enhancer have PDE4 inhibitory activity, or when only the *Sceletium* or *sceletium* extract has PDE4 inhibitory activity. For example if F1 produces response X, F2 produces response Y, then the combination of F1+F2>X+Y. In some situations F2 produces no response and the value for Y is equal to zero.

As used herein, "compounds" may be identified either by their chemical structure, chemical name, or common name. When the chemical structure, chemical name, or common name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures encompass all possible tautomeric forms of the illustrated or identified compounds. The compounds described also encompass isotopically labeled compounds where one or more atoms have an atomic mass different from the atomic mass conventionally found in nature. Examples of isotopes that may be incorporated into the compounds of the invention include, but are not limited to, $^{2}H$, $^{3}H$, $^{13}C$, $^{4}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated are congeners, analogs, hydrolysis products, metabolites and precursor or prodrugs of the compound. In general, all physical forms are equivalent for the uses contemplated herein and are intended to be within the scope of the present disclosure.

In this disclosure, "comprises," "comprising," "comprised," "containing" and "having" and the like can have the meaning ascribed to them in U.S. Patent law and can mean "includes," "including," and the like, and are generally interpreted to be open ended terms. The term "consisting of" is a closed term, and includes only the methods, compositions, components, systems, steps, or the like specifically listed, and that which is in accordance with U.S. Patent law. "Consisting essentially of" or "consists essentially" or the like, when applied to devices, methods, compositions, components, structures, steps, or the like encompassed by the present disclosure, refer to elements like those disclosed herein, but which may contain additional structural groups, composition components, method steps, etc. Such additional devices, methods, compositions, components, structures, steps, or the like, however, do not materially affect the basic and novel characteristic(s) of the devices, compositions, methods, etc., compared to those of the corresponding devices, compositions, methods, etc., disclosed herein. In further detail, "consisting essentially of" or "consists essentially" or the like, when applied to the methods, compositions, components, systems, steps, or the like encompassed by the present disclosure have the meaning ascribed in U.S. Patent law and is open-ended, allowing for the presence of more than that which is recited so long as basic or novel characteristics of that which is recited is not changed by the presence of more than that which is recited, but excludes prior art embodiments. In this specification when using an open ended term, like "comprising" or "including," it is understood that direct support should be afforded also to "consisting essentially of" language as well as "consisting of" language as if stated explicitly and vice versa. Each term provides support for the others as if expressly stated.

As used herein. "formulation" and "composition" can be used interchangeably and refer to a combination of at least two ingredients. In some embodiments, at least one ingredient may be an active agent or otherwise have properties that exert physiologic activity when administered to a subject.

As used herein, "active agent" refers to a molecule, compound, mixture, or ingredient that has a measurable physiologic effect on a subject when administered thereto in an appreciable amount, such as an effective, or therapeutically effective amount. Like terms such as "active fraction," "active component," and "active constituent" can be used interchangeable therewith.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 mg to 2.0 mg" should be interpreted to include not only the explicitly recited values of about 0.01 mg to about 2.0 mg, but also include individual values and sub-ranges within the indicated range. Thus, included in this numerical range are individual values such as 0.5 mg, 0.7 mg, and 1.5 mg, and sub-ranges such as from 0.5 mg to 1.7 mg, from 0.7 mg to 1.5 mg, and from 1.0 mg to 1.5 mg, etc. This same principle applies to ranges reciting only one numerical value. Furthermore, such an interpretation should apply regardless of the breadth of the range or the characteristics being described.

As used herein, a "derivative" is a compound obtained from a source compound an analog, homolog tautomeric form, stereoisomer, polymorph, hydrate, pharmaceutically acceptable salt or pharmaceutically acceptable solvate thereof, by a simple chemical process converting one or more functional groups, by means of oxidation, hydrogenation, alkylation, esterification, halogenation and the like. The term "analog" refers to a compound having a structure similar to that of another one, but differing from it with respect to a certain component. The compound may differ in one or more atoms, functional groups, or substructures, which may be replaced with other atoms, groups, or substructures. In one aspect, such structures possess at least the same or a similar therapeutic efficacy for a given indication. The term "tautomer" or "tautomeric form" refers to structural isomers of different energies which are interconvertible via a low energy barrier. The term "stereoisomer" refers to one of a set of isomers whose molecules have the same number and kind of atoms bonded to each other, but which differ in the way these atoms are arranged in space. The term "polymorph" refers to crystallographically distinct forms of a substance. In addition, an agent can be said to be "derived" from a source containing many compounds or agents, such as a plant, fungus, bacteria, or other organism. In this context, the agent can be described or otherwise referred to in terms of its source, rather than by its own properties, characteristics, name, or attributes per se. For example, an extract obtained from a plant may be described as "derived" from the plant.

The phrase "effective amount," "therapeutically effective amount," or "therapeutically effective rate(s)" of an active ingredient refers to a non-toxic, but sufficient amount or delivery rates of the active ingredient, to achieve therapeutic results in treating a disease or condition for which the drug is being delivered. It is understood that various biological factors may affect the ability of a substance to perform its intended task. Therefore, an "effective amount," "therapeutically effective amount," or "therapeutically effective rate(s)" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

The term "extract" includes any parts of, or a material derived from, the raw material of a particular source. Extracts may take many forms including but not limited to: solid, liquid, particulate, chopped, distillate, etc. and may be performed by any number of procedures or protocols, such as chopping, grinding, pulverizing, boiling, steaming, soaking, steeping, applying a gas, etc., and may employ any suitable reagents, such as water, alcohol, steam, or other organic materials. A wide number of extraction methods and techniques are known to those of ordinary skill in the art. In some embodiments, extracts can be made from specific parts of a source, such as the aerial parts of a plant, the roots of a plant, the mycelium of a fungus, etc. In some aspects and extract may include one or more active fractions or active agents.

As used herein, a "liquid extract" refers to those substances prepared using a solvent, e.g., ethanol, water, steam, superheated water, methanol, hexane, chloroform liquid, liquid $CO_2$, liquid $N_2$, propane, supercritical $CO_2$ or any combination thereof. Liquid extracts, as used herein, can refer to a dried powder or other solid form derived from a source using a liquid extract as a step in the overall extraction protocol. Liquid extracts typically have a given purity percentage and can be relatively to highly pure. In some aspects, the purity of an extract can be controlled by, or be a function of the extraction process or protocol.

As used herein "PDE4-associated pathologies," "PDE4 related conditions," "PDE4 related diseases," and the like are used interchangeably and refer to diseases or conditions related to or caused by the degradation of cellular cAMP by PED4. A number of exemplary PDE4 related conditions are enumerated herein.

As used herein, "oxidative stress" refers to an imbalance between the manifestation of reactive oxygen species (ROS) and a biological system's ability to readily detoxify the reactive intermediates. ROS result in the formation of free radicals. Free radicals (e.g. hydroxyl, nitric acid, superoxide) or the non-radicals (e.g. hydrogen peroxide, lipid peroxide) damage (called oxidative damage) specific molecules with consequential injury to cells or tissue. Disturbances in the normal redox state of cells can cause toxic effects through the production of peroxides and free radicals that damage all components of the cell, including proteins, lipids, and DNA. While short term oxidative stress can be beneficial; over time oxidative stress can be involved in the etiology of many diseases, such as atherosclerosis, type 1, type 2, and type 3 diabetes, Parkinson's disease, cardiac arrest, myocardial infarction, Alzheimer's disease, Fragile X syndrome, and chronic fatigue syndrome. Increasing intracellular concentrations of cAMP through the inhibition of PDE4 can have a salutary effect on cells stressed by ROS.

As used herein, "*Sceletium*" refers to a plant in the plant genus *Sceletium*, which is a member of the subfamily Mesembrvanthemaceae of the family Azioacae. *Sceletium* are low growing succulent herbs commonly found in South Africa. *Sceletium* spp. (i.e. species) include but are not limited to: *S. tortuosum, S. strictum, S. subvelutinum. S. joubertii*, and *S. namaquense.*

As used herein, "*Sceletium* extract" refers to extracts that are derived from the raw material of any part of a plant in the plant genus *Sceletium*. Extracts can be made from and/or contain the material of specific species such as *S. tortuosum, S. strictum, S. subvelutinum, S. joubertii*, and *S. namaquense* or a combination thereof. Additionally, in some embodiments, extracts can be made or derived from specific parts of a *Sceletium* plant, such as the aerial parts (i.e. above ground parts, such as leaves, flowers, fruit, stems, seeds, etc.) or the roots.

As used herein, "substantial" or "substantially" when used in reference to a quantity or amount of a material, or a specific characteristic thereof, refers to an amount that is sufficient to provide an effect that the material or characteristic was intended to provide. The exact degree of deviation allowable may in some cases depend on the specific context. Similarly, "substantially free of" or the like refers to the lack of an identified element or agent in a composition. Particularly, elements that are identified as being "substantially free of" are either completely absent from the composition, or are included only in amounts which are small enough so as to have no measurable effect on the composition.

The terms "treat." "treating," or "treatment" as used herein and as well understood in the art, mean an approach for obtaining beneficial or desired results, including without limitation clinical results in a subject being treated. Beneficial or desired results can include, but are not limited to, alleviation or amelioration of one or more signs or symptoms of a condition, diminishment of extent of disease, stabilizing (i.e. not worsening) the state of a disease or condition, delaying or slowing of disease progression, amelioration or palliation of the disease state, diminishment of the reoccurrence of disease, and remission (whether partial or total), whether detectable or undetectable. "Treat," "treating" and "treatment" can also mean prolonging survival as compared to expected survival if not receiving treatment and can be prophylactic. Such prophylactic treatment can also be referred to as prevention or prophylaxis of a disease or condition. The prophylaxis may be partial or complete. Partial prophylaxis may result in the delayed onset of a physiological condition.

As used herein, "pharmaceutically acceptable" refers generally to materials which are suitable for administration to a subject in connection with an active agent or ingredient. For example, a "pharmaceutically acceptable carrier" can be any substance or material that can be suitably combined with an active agent to provide a composition or formulation suitable for administration to a subject. Excipients, diluents, and other ingredients used in or used to prepare a formulation or composition for administration to a subject can be used with such term.

Comparative terms such as "more effectively," "greater than," "improved," "enhanced," and like terms can be used to state a result achieved or property present in a formulation or process that has a measurably better or more positive outcome than the thing to which comparison is made. In some instances comparison may be made to the prior art.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Any steps recited in any method or process claims may be executed in any order and are not limited to the order presented in the claims unless otherwise stated.

The present disclosure relates to extracts derived from the plant genus *Sceletium*. Plants of the genus *Sceletium* can be considered among the most commercially promising plants indigenous to South Africa, with potential for use in dietary supplements, natural medicines, and veterinary and pharmacologic products. *Sceletium* spp. are found throughout the southwestern portion of South Africa in arid environments and are distinguishable on the basis of different vegetative, flower, fruit, and seed characteristics.

Historically, *Sceletium* was used by local individuals in aboriginal medicinal and tribal practices. In one example, *S. tortuosum* was chewed, smoked, or used as a snuff that produced euphoria and alertness that gently fade into relaxation. Additionally, the Hottentots of Southern Africa used *S. tortuosum* as a mood enhancer, relaxant, and empathogen. When chewed in sufficient quantities *Sceletium* has mild anesthetic properties in the mouth, much like kava. *Sceletium* was used by the San tribes for tooth extraction, or in smaller doses, for children with colic. Furthermore, a tea made from *Sceletium* was sometimes used to wean alcoholics off alcohol. Moreover, *Sceletium* was used as a psychotropic in tincture form and more recently for applications in promoting a sense of well-being, relieving stress in healthy individuals and for treating clinical anxiety and depression.

Alkaloids are one type of active agent in *Sceletium*. The known alkaloids can be categorized into four groups: (1) 3a-aryl-cis-octahydroindoles (e.g., mesembrine), (2) C-secomesembrine alkaloids (e.g., joubertiamine), (3) alkaloids containing a 2,3-disubstituted pyridine moiety and two nitrogen atoms (e.g., *Sceletium* alkaloid A4), and (4) a ring C-seco *Sceletium* alkaloid A4 group (e.g., tortuosamine). The 3a-aryl-cos-octahydroindole group of alkaloids, includes mesembrine, mesembranol, and mesembranone. The pharmacologic activities of this 3a-aryl-cos-octahydroindole group of alkaloids, include anxiolytic or antianxiety effects as well as anti-depressive effects. The mesembrine-like alkaloids are have central nervous system effects which include an ability to inhibit serotonin-re-uptake (SSRI) and PDE4 activity. A standardized extract of the plant could include dual PDE4 inhibition and 5-HT reuptake inhibition, a combination that might offer potential therapeutic advantages.

While it is known that the alkaloids of *S. tortuosum* have anti-depressant or anti-anxiety effects due to the inhibition of serotonin re-uptake and PDE4 inhibition, the present inventors know of no evidence of formulations or combinations of ingredients that would enhance these activities, or otherwise enhance PDE4 inhibition relative to other PDE isozymes. Additionally, many PDE4 inhibiting compounds have narrow therapeutic windows and often cause undesirable side effects (nausea, diarrhea and headaches) at doses sufficient to have a therapeutic effect. Therefore, the present inventors have identified a need for compositions or formulations including PDE4 inhibitors that can be administered at therapeutically effective doses and do not exhibit undesirable side effects when administered at such levels.

A phosphodiesterase (PDE) is any enzyme that breaks a phosphodiester bond. The most commonly known PDEs are the cyclic nucleotide PDEs that degrade the phosphodiester bond in the second messenger molecules cAMP and cyclic guanosine monophosphate (cGMP). In doing so, PDEs regulate the localization, duration, and amplitude of cyclic nucleotide downstream signaling within subcellular domains. PDEs are therefore important regulators of signal transduction mediated by these second messenger molecules. The 21 genes of the superfamily of PDE enzymes have been classified into 11 families designated PDE1-PDE11 in mammals. This classification is based upon amino acid sequences, substrate specificities, regulatory properties, pharmacological properties, and tissue distribution. With respect to substrate specificity, PDE4, 7, and 8 are cAMP-selective hydrolases; PDE5, 6 and 9 are cGMP-selective; and PDE1, 2, 3, 10, and 11 can hydrolyze both cAMP and cGMP. The dual specificity of these later PDEs allows for cross-regulation of the cAMP and cGMP pathways.

FIG. 1 shows exemplary effects of PDE inhibition on cyclic nucleotide degradation in various tissues and physiological processes mediated by cAMP or cGMP. This modulation of the downstream signaling pathways relating to cAMP and cGMP can result in profound alterations in cellular signal transduction pathways and reflects metabolic changes associated with the specific PDE inhibitor.

Phosphodiesterase type IV (PDE4) inhibitors increase or prolong concentrations of intracellular cAMP resulting in the inhibition of PDE4 activity. Several diseases and conditions are related to processes mediated via protein phosphorylation through PDE4. These diseases and conditions include but are not limited to include: autoimmune disorders, allergic or inflammatory disorders, metabolic syndrome or diabetes associated disorders, cancer, ocular disorders, neurological disorders, mild to moderate depression, anxiety related disorders, psychological and psychiatric disorders where anxiety is present, major depressive episodes, alcohol and drug dependence, bulimia nervosa, obsessive-compulsive disorders and cognitive defects in AD.

In one exemplary invention embodiment, there is provided a PDE4 activity inhibiting formulation. The formulation comprises a *Sceletium* extract in combination with at least one activity enhancer. The combination of the activity enhancer with *Sceletium* extract can improve the PDE4 inhibiting activity to beyond the level of inhibition that is achieved by administering the *Sceletium* extract or the activity enhancer alone. In some embodiments, the combination is more effective than the additive effect achieved by administering the *Sceletium* extract or the activity enhancer alone. In some embodiments, the effect can be about 20% greater, 25% greater, 30% greater, 35% greater, 40% greater, 45% greater, 50% greater, 55% greater, 60% greater 65% greater, 70% greater, 75% greater, 80% greater, 85% greater, or even 90% greater than the inhibitory effect achieved by administering either the *Sceletium* extract or the activity enhancer alone. In other embodiments, the effect can be from about 30% to about 80% greater, from about 25% to about 75% greater, from about 35% to about 85% greater, from about 20% to about 60% greater, from about 25% to about 50% greater, or from about 30% to about 45% greater than the inhibitory effect achieved by administering either the *Sceletium* extract or the activity enhancer alone. In some embodiments, the enhanced PDE4 inhibitory effect can be synergistic.

The *Sceletium* extract can be derived from any parts of or a material derived from the raw materials of a *Sceletium* species. In one exemplary embodiment, the *Sceletium* extract is from at least one of: *S. tortuosum, S. strictum, S. subvelutinum, S. joubertii, S. namaquense* or a combination thereof. In another embodiment, the *Sceletium* extract can be derived from *S. tortuosum*. In some embodiments, the extract can be derived from aerial portions of the *Sceletium* plant. In other embodiments the extract can be derived from the plants roots, stems, leaves, flowers, or a combination thereof. The extract can be a liquid extract, a powder, a compound, or a mixture thereof. The *Sceletium* extract can be present in the formulation in an amount of from about 1 wt % to about 50 wt %, from about 1 wt % to about 25 wt %, from about 2.5 wt % to about 20 wt %, or from about 3 wt % to about 15 wt %.

In some embodiments, at least one activity enhancer is combined with the *Sceletium* extract in the formulation. The activity enhancer can be any compound that increases PDE4 inhibition when combined with *Sceletium* extract. The activity enhancer can be in the form of an extract, compound, mineral, pharmaceutically acceptable salt, or any other form that is suitable of being placed in a desired formulation. In some embodiments, the activity enhancer is incapable or substantially incapable of inhibiting PDE4 activity on its own.

A wide range of compounds and agents can be used as activity enhancers for the *Sceletium* extract. In one embodiment, the activity enhancer can be an amino acid or an amino acid analog. Exemplary amino acids include without limitation, L-theanine, theanine, L-glutamic acid, L-L glutamate, L-glutamine, alanine, arginine, asparagine, ethylamine, glutamate, glutamine, histidine, isoleucine, leucine, lysine, methionine, phenylalanine, serine, threonine, tryptophan, tyrosine, and valine. In another embodiment, the activity enhancer can be a metal or a compound having a metal. Exemplary metals and metal compounds include without limitation, magnesium, calcium, strontium, zinc, magnesium carbonate, magnesium chloride, magnesium citrate, magnesium, hydroxide, magnesium oxide, magnesium sterate, magnesium sulfate, calcium citrate, calcium gluconate, calcium phosphate, calcium stearate, zinc acetate, zinc gluconate, zinc oxide, and zinc sulfate. In yet another embodiment, the activity enhancer can be a vitamin, an analog of a vitamin, a salt of a vitamin, or a phosphorylated derivative of a vitamin. Exemplary vitamins include without limitation, acefurtiamine, acetiamine, allithiamine, beclotiamine, benfotiamine, bentiamine, bisbentiamine, cetotoiamine, cycotiamine, fursultiamine, monophosphothiamine, octotiamine, prosultiamine, sulbutiamine, vintiamol, adenosine thiamine diphosphate, adenosine thiamine triphosphate, thiamine diphosphate, thaimine mononitrate, thiamine monophosphate, thiamine triphosphate, adenine, adenylic acid, biotin, catechol, cobalamins, folic acid, niacin, nicotinic acid, pantothenic acid, pyridoxine, pyridoxal, pyridoxamine riboflavin, thiamine, retinol, ascorbic acid, calciferol, tocopherol, and phylloquinone. In a further embodiment, the activity enhancer can be a polysaccharide. Exemplary polysacharides include without limitation, arabinoxylans, cellodextrins, cellulose, glycogen, hemicellulose, pectins, and starch. In one exemplary embodiment, the activity enhancer can be any member selected from the group consisting of: L-theanine, thiamine, zinc gluconate, magnesium citrate, magnesium stearate, cellulose, or mixtures thereof. In another embodiment, the activity enhancer is L-theanine. In yet another embodiment, the activity enhancer is thiamine. In a further embodiment, the formulation comprises a plurality of activity enhancers. The plurality of activity enhancers can include any combination of the activity enhancer types (i.e. amino acids, metals, vitamins, and polysaccharides) discussed above. In one embodiment, the activity enhancers can include L-theanine and thiamine. In another embodiment, the activity enhancers can include L-theanine, thiamine, magnesium citrate, and zinc. In an additional embodiment, the activity enhancer can include L-theanine, thiamine, magnesium citrate, zinc, and magnesium stearate. The amount of activity enhancer can be selected in view of the specific compound used and the desired properties of the final formulation. However, in one embodiment, the activity enhancer can be present in the formulation in an amount of from about 1 wt % to about 90 wt %, from about 5 wt % to about 85 wt %, from about 10 wt % to about 80 wt %, from about 1 wt % to about 75 wt %, or from about 1 wt % to about 50 wt %.

In one exemplary embodiment, the Sceletium extract is present in the formulation in an amount of from about 1 wt % to about 50 wt % and the at least one activity enhancer is present from about 1 wt % to about 90 wt % in the formulation. In another embodiment, the Sceletium extract is present from about 1 wt % to about 25 wt % and the at least one activity enhancer is present from about 5 wt % to about 85 wt % in the formulation. In yet another embodiment, the Sceletium extract is present from about 2.5 wt % to about 20 wt % and the at least one activity enhancer is present from about 1 wt % to about 50 wt % in the formulation. In a further embodiment, the Sceletium extract is present from about 3 wt % to about 15 wt % and the at least one activity enhancer is present from about 1 wt % to about 75 wt % in the formulation.

The formulation can include various ratios of the activity enhancer to the Sceletium extract. In one example, the weight ratio of amount of the activity enhancer to the amount of the Sceletium extract can be from about 1:1 to about 20:1. In another example, the weight ratio of the amount of the activity enhancer to the amount of the Sceletium extract can be from about 2:1 to about 15:1. In a further embodiment, the weight ratio of the amount of the activity enhancer to the amount of the Sceletium extract can be from about 1:1 to about 1:20. In yet another example, the weight ratio of the amount of the activity enhancer to the amount of the Sceletium extract can be from about 0.25:1 to about 20:1. In yet another example, the weight ratio of the amount of the activity enhancer to the amount of the Sceletium extract can be from about 2.5:1 to about 14:1. In yet still another example, the weight ratio of the amount of the activity enhancer to the amount of the Sceletium extract can be from about 0.25:10 to about 14:1.

In some embodiments, the formulation can include a pharmaceutically acceptable carrier. While the type of pharmaceutically acceptable carrier/vehicle employed in generating the disclosed formulations can vary depending upon the mode of administration of the composition, generally pharmaceutically acceptable carriers are physiologically inert and non-toxic. In some embodiments, the pharmaceutically acceptable carrier can be a pharmaceutical grade compound. Exemplary suitable carriers include water, magnesium carbonate, talc, sugar, lactose, pectin, dextrin, starch (from corn, wheat, rice, potato, or other plants), gelatin, tragacanth, a low melting wax, cocoa butter, sucrose, mannitol, sorbitol, cellulose (such as methyl cellulose, hydroxypropylmethyl-cellulose, or sodium carboxymethylcellulose), and gums (including arabic and tragacanth), as well as proteins such as gelatin and collagen. In one embodiment, the carrier can comprise cellulose, gelatin, water, or a mixture thereof.

In some embodiments, the formulations can comprise pharmaceutically acceptable excipients. Exemplary pharmaceutically acceptable excipients can be selected from the group consisting of coatings, isotonic and absorption delaying agents, binders, adhesives, lubricants, disintergrants, coloring agents, flavoring agents, sweetening agents, absorbents, detergents, and emulsifying agents. When the formulation includes an emulsifying agent, the emulsifiers can be added to improve the stability of the final product. Exemplary emulsifiers include, but are not limited to, lecithin (e.g., from egg or soy), or mono- and di-glycerides. Other emulsifiers are readily apparent to the skilled artisan and selection of suitable emulsifier(s) will depend, in part, upon the formulation and final product.

Various formulation embodiments can further include flavorings, coloring agents, spices, nuts, preservatives, antioxidants, vitamins, minerals, proteins, fats, and/or carbohydrates. The amount of other ingredients can vary based on the particular design, intended dosage, and method of administration. The total amount of other ingredients can also depend, in part, upon the condition and weight of the subject.

Flavors, coloring agents, spices, nuts and the like can be incorporated into the product. Flavorings can be in the form of flavored extracts, volatile oils, chocolate flavorings (e.g., non-caffeinated cocoa or chocolate, chocolate substitutes such as carob), peanut butter flavoring, cookie crumbs, crisp rice, vanilla or any commercially available flavoring. Flavorings can be protected with mixed tocopherols. Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedar wood oil, cherry oil, walnut oil, cinnamon oil, clove oil, or peppermint oil; peanut butter, chocolate flavoring, vanilla cookie crumb, butterscotch or toffee. In one embodiment, the formulation can contain berry or other fruit flavors. The food compositions may further be coated, for example with a yogurt coating.

Preservatives can be added to the formulation to extend the shelf life of the product. Exemplary preservatives include potassium sorbate, sodium sorbate, potassium benzoate, sodium benzoate, or calcium disodium EDTA.

The formulation can also include natural or artificial sweeteners. In one embodiment, the potential sweeteners can include glucose, sucrose, fructose, saccharides, cyclamates, aspartamine, sucralose, aspartame, acesulfame K, sorbitol, or a combination thereof.

The formulation can further include pharmaceutically acceptable forms of vitamins, minerals, and other nutrients. The nutrients chosen for inclusion in the formulation can vary depending on the particular design, intended dosage, method of administration, and condition of the subject. Individuals skilled in the art are aware of vitamins, minerals, and other nutrients that can be incorporated into formulations and how to incorporate these.

The components in the formulation can be included as salts. In particular, pharmaceutically acceptable salts of the components are contemplated. A "pharmaceutically acceptable salt" is a combination of a compound and either an acid or a base that forms a salt (such as, for example, the magnesium salt, denoted herein as "Mg" or "Mag") with the compound. Pharmaceutically acceptable salts can be tolerated by a subject under therapeutic conditions. In general, a pharmaceutically acceptable salt of a compound will have a therapeutic index (the ratio of the lowest toxic dose to the lowest therapeutically effective dose) of 1 or greater. Those skilled in the art recognize that the lowest therapeutically effective dose will vary from subject to subject and from indication to indication, and will thus adjust the formulation accordingly.

The formulation can be provided in any convenient form. When the formulation is formulated in an oral dosage form, the formulation can comprise a capsule, tablet, powder, suspension, gel, liquid, beverage, syrup, or a food. In one embodiment, the formulation may be formulated as powder that can be mixed with consumable liquids, such as milk, juice, sodas, water, or consumable gels or syrups for mixing into other nutritional liquids or foods. The formulation can also be formulated to include pre-measured supplemental foods, such as single serving beverages or bars. In one embodiment, the formulation can be formulated into a nutritional beverage. In yet other embodiments, the formulation can be made in a variety of forms, such as pudding, confections (i.e., candy), ice cream, frozen confections and novelties, or non-baked, extruded food products such as bars. In one embodiment, the manufacture of a food bar can comprise adding the dry ingredients with the liquid ingredients in a mixer and mixing until the dough phase is reached; the dough is then put into an extruder and extruded; the extruded dough is then cut into appropriate lengths, and the product is left to cool. The formulation can also be provided as a cream or lotion for topical application. One trained in the art can readily formulate the present composition into any of these convenient forms for oral or topical administration.

When formulated in an oral dosage form, the formulation can comprise from about 0.01 mg to about 30,000 mg, from about 0.01 mg to about 10,000 mg, from about 0.01 mg to about 5,000 mg, or from about 0.01 mg to about 100 mg of the *Sceletium* extract.

Also, presented herein is a *Sceletium* extract dosage form for administration to a subject to inhibit phosphodiesterase type IV (PDE4) activity. The extract dosage includes an amount of a *Sceletium* extract and an amount of at least one activity enhancer. The dosage form when administered to a subject is more effective at inhibiting PDE4 than either the amount of *Sceletium* extract or the amount of the activity enhancer alone. While the dosage form can vary, the dosage form can be made appropriate to the route of administration, the disease or condition being treated, and the subject.

The *Sceletium* extract in the dosage form, can be as described above, and comprise any parts of or material derived from the raw materials of a *Sceletium* species. In one exemplary embodiment, the *Sceletium* extract in the dosage form is from at least one of *S. tortuosum, S. strictum, S. subvelutinum, S. joubertii,* and *S. namaquense* or a combination thereof. The *Sceletium* extract in the dosage form can be present in a therapeutically effective amount without the activity enhancer, or the *Sceletium* extract can be present in an amount that is not therapeutically effective without the activity enhancer. In other words, the *Sceletium* extract can be in an amount that is insufficient to provide a therapeutic effect, but with the presence of the activity enhancer, the amount may become sufficient to have a therapeutic effect due to the increased activity provided by the activity enhancer.

The amount of the *Sceletium* extract in the dosage can vary from about 0.01 mg to about 30,000 mg, from about 0.01 mg to about 10,000 mg, from about 0.01 mg to about 5,000 mg, or from about 0.01 mg to about 100 mg. In another embodiment, the amount of the *Sceletium* extract in the dosage can vary from about 0.1 mg to about 100 mg, from about 0.1 mg to about 1,000 mg, from about 0.1 mg to about 5,000 mg, from about 0.1 mg to about 10,000 mg, from about 0.25 mg to about 100 mg, from about 0.25 mg to about 1,000 mg, from about 0.25 mg to about 5,000 mg, from about 0.25 mg to about 10,000 mg, from about 0.5 mg to about 100 mg, from about 0.5 mg to about 1,000 mg, from about 0.5 mg to about 5,000 mg, or from about 0.5 mg to about 10,000 mg. In a further embodiment, the amount of the *Sceletium* extract in the dosage form can vary from about 1 mg to about 100 mg, from about 1 mg to about 1,000 mg, from about 1 mg to about 5,000 mg, from about 1 mg to about 10,000 mg, or from about 1 mg to about 30,000 mg.

In one embodiment, the *Sceletium* extract can have a standardized alkaloid content, such as total alkaloids. In one example, the content can be from about 1 mg to about 300 mg. In another example, the amount can be from about 5 mg to about 200 mg. In a further example, the amount can be from about 10 mg to 100 mg. In yet another example, the amount can be from about 20 mg to about 30 mg. In another example, the alkaloid content can be standardized at about 25 mg.

The activity enhancer can be in the form of an extract, compound, mineral, pharmaceutically acceptable salt, or any other suitable form capable of being placed in the dosage form, and can be any compound or agent suitable for use as an activity enhancer for a *Sceletium* extract, including the exemplary compounds and agents recited herein. In one exemplary embodiment, the activity enhancer can be a member selected from the group consisting of: L-theanine, thiamine, zinc gluconate, magnesium citrate, magnesium stearate, cellulose, or a mixture thereof. The amount of the activity enhancer in the dosage form can vary from about 0.01 mg to about 60,000 mg, from about 0.01 mg to about 40,000 mg, from about 0.01 mg to about 20,000 mg, from about 0.01 mg to about 10,000, from about 0.01 mg to about 5,000 mg, from about 0.01 mg to about 1,000 mg, or from about 0.01 mg to about 125 mg. In another embodiment, the amount of the activity enhancer in the dosage form can vary from about 0.1 mg to about 150 mg, from about 0.1 mg to about 1,000 mg, from about 0.1 mg to about 5,000 mg, from about 0.1 mg to about 10,000 mg, from about 0.25 mg to about 150 mg, from about 0.25 mg to about 1,000 mg, from about 0.25 mg to about 5,000 mg, from about 0.25 mg to about 10,000 mg, from about 0.5 mg to about 150 mg, from about 0.5 mg to about 1,000 mg, from about 0.5 mg to about 5,000 mg, or from about 0.5 mg to about 10,000 mg. In a further embodiment, the amount of the activity enhancer extract in the dosage can vary from about 1 mg to about 125 mg, from about 1 mg to about 500 mg, from about 1 mg to about 1,000 mg, from about 1 mg to about 5,000 mg, from about 1 mg to about 10,000 mg, or from about 1 mg to about 60,000 mg. These amounts can be for a single activity enhancer, or for a combination thereof.

In one exemplary embodiment, the *Sceletium* extract is present from about 1 mg to about 100 mg and the at least one activity enhancer is present from about 1 mg to about 125 mg. In another embodiment, the *Sceletium* extract is present from about 0.01 mg to about 10,000 mg and the at least one activity enhancer is present from about 0.01 mg to about 10,000 mg. In yet another embodiment, the *Sceletium* extract is present from about 1 mg to about 30,000 mg and the at least one activity enhancer is present from about 1 mg to about 60,000 mg. In a further embodiment, the *Sceletium* extract is present from about 0.25 mg to about 1,000 mg and the at least one activity enhancer is present from about 0.25 mg to about 5,000 mg.

The dosage form can be administered using a dosage unit according to a pre-determined regimen. The term "dosage unit" is understood to mean a unitary, i.e. a single dose which is capable of being administered to a patient. The dosage unit can be readily handled and packed, while remaining as a physically and chemically stable unit dose comprising either the active ingredient or a mixture of active ingredient(s) with a solid or liquid pharmaceutical vehicle. The pre-determined regimen can be administered once per day or multiple times per day. When the regimen is administered multiple times per day, the regimen can be administered once per day, twice per day, three times per day, four times per day, or five times per day. The regimen could also be administered on an every other day, every three days, every five days, every week, every other week or on a monthly basis. The exact regimen can vary based on the amounts of *Sceletium* extract and activity enhancer in the dosage form, the disease be treated, and the subject's individual characteristics and needs. In some embodiments, the dosing regimen can be on an "as needed" basis. For example, at the time a subject perceives the onset of signs or symptoms of a condition (i.e. an anxiety episode), the subject can administer a suitable dose. In alternative embodiments, the dose can be taken according to a specific pre-set regimen as mentioned herein.

The dosage form can be in any of a wide variety of forms. The dosage form can be an oral, transdermal, transmucosal, inhalation, rectal, ophthalmic (including intra-vitreal or intracameral), nasal, topical (including buccal and sublingual), vaginal, or parenteral (including subcutaneous, intramuscular, intravenous, intra-dermal, and intra-tracheal) dosage form. When the dosage form is an oral dosage, the formulation can be in the form of discrete units such as capsules, sachets, tablets, soft gels or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. The active ingredient may also be administered in the form of a bolus, electuary or paste. When the dosage form is in the form of a depot, the formulation may be administered by implantation (e.g. subcutaneously, intra-abdominally, or intramuscularly) or by intramuscular injection. Thus, for example, the active ingredient may be formulated with suitable polymeric or hydrophobic materials (for example, as an emulsion in a pharmaceutically acceptable oil), or an ion exchange resin. In addition, the dosage form can be in the form of a sustained release formulation. In one exemplary embodiment, polymers or other ingredients can be added to create the sustained release dosage form.

Also presented herein are methods of inhibiting phosphodiesterase type IV (PDE4) activity in a subject. Such methods generally comprise administering an amount of *Sceletium* extract and at least one activity enhancer to a subject. As discussed above, the *Sceletium* extract is any part of or a material derived from the raw materials of a *Sceletium* species. Also as discussed above, the activity enhancer is any agent that increases PDE4 inhibition when combined with *Sceletium* extract. In one exemplary embodiment, the activity enhancer can be a member selected from the group consisting of: L-theanine, thiamine, zinc gluconate, magnesium citrate, magnesium stearate, cellulose, or mixtures thereof. The activity enhancer is any agent that increases PDE4 inhibition when combined with *Sceletium* extract. In some embodiments of the method, the inhibiting effect is greater than an inhibitory effect provided by either the amount of the *Sceletium* extract or the amount of activity enhancer alone. In one embodiment, the *Sceletium* extract is present in a therapeutically effective amount, and in another embodiment it is present in an amount that becomes therapeutically effective in the presence of the activity enhancer.

In some embodiments, the formulations and dosage forms can be used to provide treatment of a subject that displays or anticipates signs or symptoms of a disease or condition selected from the group consisting of: anxiety related disorders, depression related disorders, allergic disorders, autoimmune disorders, diabetes associated disorders, inflammatory conditions, neurological disorders, or cardiovascular diseases. In one exemplary embodiment the disease or condition is an anxiety related disorder. In another exemplary embodiment, the disease or condition is a depression related disorder.

Allergic disorders refer to those conditions and/or diseases that are related to PDE4 activity. Allergic disorders can be an exaggerated or pathological reaction (as by sneezing, respiratory distress, itching, or skin rashes) to substances, situations, or physical states that are without comparable effect on the average individual.

Autoimmune diseases result from a dysfunction of the immune system in which the body produces autoantibodies that attack its own organs, tissues and cells. Autoimmune diseases can be process mediated via protein phosphorylation through PDE4.

Diabetes associated disorders refers to insulin related disorders. Insulin related disorders are diseases or conditions where the response to insulin is either causative of the disease or has been implicated in the progression or suppression of the disease or condition. Representative examples of insulin related disorders include, without limitation diabetes (both type 1 and type 2), diabetic complications, insulin sensitivity, polycystic ovary disease, hyperglycemia, dyslipidemia, insulin resistance, metabolic syndrome, obesity, body weight gain, inflammatory diseases, diseases of the digestive organs, stenocardia, myocardial infarction, sequelae of stenocardia or myocardial infarction, senile dementia, and cerebrovascular dementia.

Inflammatory conditions are local responses to cellular injury that are marked by capillary dilatation, leukocytic infiltration, redness, heat, pain, swelling, and/or loss of function. Inflammatory conditions serve as a mechanism initiating the elimination of noxious agents and of damaged tissue. Systemic inflammatory responses can produce "flu-like" symptoms, such as, for instance, fever, chills, fatigue/loss of energy, headaches, loss of appetite, and muscle stiffness. Examples, without limitation, of inflammatory conditions include diseases of the digestive organs (such as ulcerative colitis, Crohn's disease, pancreatitis, gastritis, benign tumor of the digestive organs, digestive polyps, hereditary polyposis syndrome, colon cancer, rectal cancer, stomach cancer and ulcerous diseases of the digestive organs), stenocardia, myocardial infarction, sequelae of stenocardia or myocardial infarction, senile dementia, cerebrovascular dementia, immunological diseases and cancer in general.

Neurological disorders refer to any disturbance in the structure or function of the central nervous system resulting from developmental abnormality, disease, injury or toxin. Representative, non-limiting examples of neurological disorders include Alzheimer's disease, type 3 diabetes, Parkinson's disease, multiple sclerosis, amyotrophic lateral sclerosis (ALS or Lou Gehrig's Disease), Huntington's disease, neurocognitive dysfunction, senile dementia, and mood disorder diseases.

Cardiovascular diseases refer to those pathologies or conditions that impair the function of, or destroy cardiac tissue or blood vessels.

The methods disclosed can be used on any subject that would benefit from PDE4 inhibition. In one exemplary embodiment, the subject is a mammal. In another embodiment mammals include humans. In other exemplary embodiments, mammals include non-human mammals. Non-human mammals can include domesticated animals, such as cats and dogs, as well as farm animals such as horses and cows, mice, and rats.

In one embodiment, the present formulations and dosage forms can be administered to a subject that is suffering from a PDE4 related condition or disease, or the method can be administered prophylactically in order to prevent the occurrence or progression of a PDE4 related condition or disease. The formulation or dosage used can be administered in the form of an oral, transdermal, transmucosal, rectal, ophthalmic (including intravitreal or intracameral), nasal, nasal by inhalation, topical (including buccal and sublingual), vaginal, parenteral (including subcutaneous, intramuscular, intravenous, intradermal, and intratracheal), by implantation, or intramuscularly. In one exemplary embodiment the method administers the formulation orally. The method can include administering the Sceletium extract and the at least one activity enhancer concurrently. When administered concurrently, the Sceletium extract and at least one activity enhancer can be administered from a single formulation. In another embodiment, the Sceletium extract and at least one activity enhancer are administered separately. In yet another embodiment, the Sceletium extract and the at least one activity enhancer are administered sequentially.

In one embodiment a method of treating a PDE4 related condition in a subject can comprise administering an amount of a Sceletium extract and an activity enhancer. In one embodiment, the amount of Sceletium extract per dose can be about 25 mg and the daily amount of the activity enhancer per dose can be about 515 mg. In another embodiment, the amount of the Sceletium extract per dose can be about 30 mg and the amount of the activity enhancer per dose can be about 60 mg. In yet another embodiment, the amount of the Sceletium extract per dose can be about 100 mg and the amount of the activity enhancer per dose can be about 125 mg. In a further embodiment, the amount of the Sceletium extract per dose can be about 100 mg and the amount of the activity enhancer per dose can be about 4,000 mg. While exemplary dosage amounts are presented above, the exact dosage amount will vary based on the disease or condition being treated and the individual needs and characteristics of the subject.

In an additional invention embodiment, there is presented a method of increasing the phosphodiesterase type IV (PDE4) inhibition activity of an amount of a Sceletium extract. In one aspect, such a method comprises adding or combining an amount of at least one activity enhancer with the administration of the Sceletium extract. The Sceletium extract and the activity enhancer can be included in the method as described above. The combination of the Sceletium extract and the activity enhancer inhibits PDE4 activity to a greater degree than the amount of the Sceletium extract alone. In some embodiments, the increase in inhibition attained can be greater than the additive effect of each ingredient alone (i.e. synergistic). In one embodiment, the Sceletium extract and activity enhancer can be combined in a single formulation, or can be in separate formulations that are combined upon administration to the subject. For example, the Sceletium and activity enhancer can be administered to a subject in such a manner that they combine or effectively combine in vivo. In one embodiment, they Sceletium extract and the activity enhancer can be administered concurrently. In another embodiment they can be administered sequentially or otherwise at separate times as long as they are still able to provide the enhanced PDE4 inhibitory effect.

Further presented is a phosphodiesterase type IV (PDE4) inhibiting system. The inhibiting system comprises an amount of a Sceletium extract and an amount of at least one activity enhancer. Presented more fully above, are exemplary embodiments of the Sceletium extract and the activity enhancer use in the system, as well as, the PDE4 inhibiting activity of the system, for example the dosages and formulations set forth. The Sceletium extract and the activity enhancer can be separately assembled in the system. In some embodiments the Sceletium extract and activity enhancer are in separate formulations. When the Sceletium extract and activity enhancer are in separate formulations they can be packaged together or packaged individually. In other embodiments, the Sceletium extract and activity enhancer are in a single formulation. Regardless of the embodiment, the formulation can be in a form that masks the taste of the Sceletium extract and/or the activity enhancer (e.g., capsule or pill form) rather than incorporating them into a food or beverage (e.g., powder or bar). Separate formulations or dosages of Sceletium extract and activity enhancer can each include numerous other ingredients, such as carriers, excipients, etc.

The system can optionally include additional components. In one embodiment, the system can be associated a container(s). In some embodiments, the system can include a notice in the form prescribed by a government agency regulating the manufacture, use or sale of pharmaceutical products, which notice reflects approval by the agency of manufacture, use of sale for human administration. Furthermore, the system can be labeled with information (i.e. instructions) regarding mode of administration, sequence of administration (e.g., separately, sequentially or concurrently), or the like. Alternatively, such information can be included in a sheet or booklet separate from the product label. The system can also include means for reminding the patient to take the *Sceletium* extract and activity enhancer. The system can be a single unit dosage of the *Sceletium* extract and activity enhancer or it can be a plurality of unit dosages.

Further presented is a method for modulating protein kinase activity in a subject. As previously discussed PDE4 inhibitors can prolong or enhance the effects of a variety of physiological processes mediated by cAMP. The process can occur in a wide range of tissues through inhibition of cyclic nucleotide degradation. The modulation of the downstream signaling pathways relating to cAMP directly affects protein kinase activity. Certain protein kinases are only activated when cAMP is present. Therefore, the formulations previously discussed can be used in a method for modulating protein kinase activity.

The method includes administering to a subject a formulation having an amount of *Sceletium* extract in combination with an amount of at least one activity enhancer. The *Sceletium* extract and activity enhancer are included in the formulation as discussed above. In one embodiment when the formulation is administered to a subject, the formulation is more effective at modulating protein kinase activity then either the amount of *Sceletium* extract or the amount of activity enhancer alone. In one embodiment, the protein kinase activity that is modulated is a protein kinase selected from the group consisting of ABL, AKT, AURORA, CDK, DBF2/20, EGFR, EPH/ELK/ECK, ERK/MAPKFGFR, GSK3, IKKB, INSR, JAK DOM 1/2, MARK/PRKAA, MEK/STE7, MEKK/STE11, MLK, mTOR, PAK/STE20, PDGFR, PI3K, PKC, POLO, SRC, TEC/ATK, and ZAP/SYK. In a second embodiment, the protein kinase activity that is modulated is a protein kinase selected from the group consisting of CLK1, Met, Syk, Aurora, PRAK, Flt4, TrkC, CK2α2, MSSk1, Fms, and GSK3. Regulation of protein kinase activity is useful as a treatment for disease states or conditions because of the relationship between protein kinase activity and disease states and conditions. While not being bound by theory, it is believed that the relationship is either causative of the disease or intimately related to the expression and progression of disease-associated symptomology and pathology.

Further presented is a method of preparing a PDE4 inhibiting formulation. The method includes combining the *Sceletium* extract with at least one activity enhancer in a manner suitable for administration to a subject. The *Sceletium* extract with at least one activity enhancer includes those extracts and enhancers as previously discussed above. The method includes method of formulating compositions that are well known in the art. All methods include the step of bringing the active ingredient into association with the vehicle that constitutes one or more auxiliary constituents. In one embodiment, the method can include acquiring a source of a *Sceletium* extract and formulating the *Sceletium* extract with the activity enhancer(s). The formulation can be further formulated with a pharmaceutically acceptable carrier and/or other excipients, preservatives or additives. In one embodiment, the method further includes the step of extracting the *Sceletium* extract from a *Sceletium* sp. or spp. prior to combining the *Sceletium* extract with the activity enhancer(s). The *Sceletium* sp. or spp. can be extracted using any known extraction methods. When the extraction is a liquid extraction the extraction can occur using any suitable solvent including, organic solvents, inorganic solvents, ethanol, water, steam, superheated water, methanol, ethanol, hexane, chloroform liquid, liquid $CO_2$, liquid $N_2$, propane, supercritical $CO_2$ or any combination thereof. In a further embodiment, the material that the *Sceletium* extract is derived from can be milled prior to being extracted.

Embodiments of the present disclosure will be described with reference to the following Examples which are provided for illustrative purposes only and should not be used to limit the scope of or construe the invention.

EXAMPLES

Example 1

Formulation of *S. tortuosum*

Dry aerial parts of *S. tortuosum* were cultivated and prepared commercially by HG&H Pharmaceutical (Pty) Ltd, South Africa. The air dried *S. tortuosum* was milled using a conventional industrial milling machine. The milling occurred in a hammer mill with a mesh size adjusted to achieve a particle size >85 microns and <3 mm. The milled powder was added to an aqueous ethanoic solution comprising 70% ethanol. The ratio of raw milled plant material to extraction liquid was 1:6 w/w. The solution and milled powder were stirred with an electric stirrer. The temperature of the solution was maintained between 25° C.-50° C. and was continually and slowly stirred for 24 hours. Following the stirring, the solution was filtered through a commercial filter with an appropriate mesh size to yield the desired filtrate. The filtrate was spray-dried onto lactose monohydrate.

Example 2

Phosophodiesterase Inhibition

The ethanoic extract of *S. tortuosum* was tested for the capacity to inhibit four phosphodiesterases in a concentration dependent manner. The sample was tested at 10 concentrations with 2-fold serial dilutions starting at 125 μg/mL. Each assay was accompanied by a dose-response series of the control compound 3-isobutyl-1-methylxanthine (IBMX); positive controls were also tested at 10-concentrations with 3-fold serial dilutions starting at 100 μM.

The incubation mixture contained 10 mM Tris, pH 7.5, 5 mM MgCl2, 0.01% Brij 35, 1 mM dithiothreitol, and 1% dimethylsulfoxide (DMSO). For PDE1A, 0.2 mM $CaCl_2$ and 0.36 μM calcium/calmodulin were included in the reaction mixture. Test material was added in DMSO, followed by addition of cAMP to a final concentration of 1 μM. After one hour at ambient temperature, the reaction was stopped by the addition of a proprietary Stop/detection mixture. Fluorescence polarization was measured after another 90 minutes incubation at room temperature. AMP was quantified for each concentration using the Transcreener® fluorescence polarization assay (BellBrook Labs, Madison, Wis.) with Ex=620 nm FP and Em=688 nm P and S.

The $IC_{50}$ values (concentrations producing half maximal inhibition of control specific activity) and Hill coefficients were determined by non-linear regression analysis of the inhibition curves using Hill equation curve fitting (Y=D+ [(A−D)/(1+C/C$_{50}$)$^{nH}$)] using GraphPad Prism software (GraphPad Software, La Jolla, Calif.). Curve fits were performed from the point where the inhibitory activity at the highest concentration of compound was less than 65%. $IC_{50}$ values are presented in Table A as µg sample/mL.

TABLE A

Median Inhibitory Concentration of S. tortousum against PDE1A, PDE2A, PDE3A and PDE4D

| | Median Inhibitory Concentration | | |
|---|---|---|---|
| | $IC_{50}$ Value S. tortuosom | Controls | |
| Enzyme | µg/ML | Test Material | µg/mL |
| PDE1A | — | IBMX | 0.140 |
| PDE2A | — | IBMX | 1.78 |
| PDE3A | 124 | IBMX | 0.591 |
| PDE4D | 16.7 | IBMX | 5.63 |

The organic extract of S. tortuosum, exhibited a concentration-dependent inhibition of both PDE3A and PDE4D.

Example 3

Formulations of Sceletium Enhanced by L-theanine and Thiamine

L-theanine and thiamine were purchased from commercial sources. Independent testing of L-theanine and thiamine for PDE-inhibitory activity revealed that neither compound possessed inhibitory activity against any of the four PDE isozymes. Preparation of the alcoholic extract of S. tortuosum was performed as described in Example 1 and combined with the L-theanine and thiamine. The formulation contained 50 mg of the S. tortuosum extract, 52 mg of L-theanine, and 6.25 mg of thiamine.

Example 4

Phosphodiesterase Inhibition by Formulations Containing Sceletium, L-theanine and Thiamine The effects of formulations containing S. tortuosum extract, L-theanine, and thiamine on the inhibition of PDE4 compared to the S. tortuosum extract alone were tested. An additional objective was to observe the effects of the multi-component formulation on PDE1A, PDE2A, and PDE3A.

Enzyme assays and calculations were performed as previously described in Example 2 using the formulations prepared in Example 3. Activities were based on S. tortuosum sample content of the reaction mixture, as all other components had demonstrated no effect on PDEs and the alkaloid content of the S. tortuosum and the test formulation of S. tortuosum containing L-theanine and thiamine were balanced.

TABLE B

Median Inhibitory Concentrations of S. tortousum, L-theanine, and thiamine against PDE1A, PDE2A, PDE3A and PDE4D

| | Median Inhibitory Concentration | | | | | |
|---|---|---|---|---|---|---|
| | $IC_{50}$ Value | | | | | |
| Enzyme | S. tortuosum extract | L-theanine* | Thiamine* | S. tortousum, L-theanine, and thiamine sample | Controls Test Material | µg/mL |
| PDE1A | — | 0 | 0 | — | IBMX | 0.795 |
| PDE2A | — | 0 | 0 | — | IBMX | 1.41 |
| PDE3A | — | 0 | 0 | — | IBMX | 0.869 |
| PDE4D | 6.94 | 0 | 0 | 4.43 | IBMX | 3.24 |

*L-theanine and thiamine were tested individually at a different date for their PDE4 inhibitory effect. During that testing L-theanine and thiamine did not exhibit any inhibitory activity.

The extract combining the S. tortuosum, with L-theanine and thiamine exhibited a 36% inhibition in the PDE4 activity which is synergistic and unexpected in view of the fact that L-theanine and thiamine do not exhibit any PDE4 inhibitory activity when administered alone. The addition of L-theanine and thiamine to the S. tortuosum preparation unexpectedly increased the PDE4 inhibitory activity 1.57-fold relative to the extract alone.

Exemplary Embodiments

The following exemplary invention embodiments pertain to further aspects of the disclosure.

In one example there is provided, a phosphodiesterase type IV (PDE4) activity inhibiting formulation, comprising:
  a Sceletium extract in combination with at least one activity enhancer, wherein when administered to a subject, the formulation is more effective at inhibiting PDE4 activity than either the Sceletium extract or the activity enhancer alone.

In one example the PDE4 inhibiting effect of the formulation on the subject is more than an additive effect achieved by administering the Sceletium extract or the activity enhancer alone.

In one example, the PDE4 inhibiting effect of the formulation on the subject is from about 30% to about 80% greater than that achieved by administering either the Sceletium extract or the activity enhancer alone.

In one example, the Sceletium extract in the formulation is from at least one of S. tortuosum, S. strictum, S. subvelutinum, S. joubertii, and S. namaquense or a combination thereof.

In one example, the Sceletium extract in the formulation is derived from S. tortuosum.

In one example the Sceletium extract in the formulation is derived from aerial portions of a Sceletium plant.

In one example, the Sceletium extract comprises from about 1 wt % to about 50 wt % of the formulation.

In one example, the Sceletium extract comprises from about 3 wt % to about 15 wt % of the formulation.

In one example, the activity enhancer has substantially no PDE4 inhibitory effect of its own.

In one example, the activity enhancer in the formulation is a member selected from the group consisting of: L-theanine, thiamine, zinc gluconate, magnesium citrate, magnesium stearate, cellulose, or a mixture thereof.

In one example, the activity enhancer in the formulation is L-theanine.

In one example, the activity enhancer in the formulation is thiamine.

In one example, the formulation comprises a plurality of activity enhancers.

In one example the formulation comprises a plurality of activity enhancers and the activity enhancers include L-theanine and thiamine.

In one example, the formulation comprises a plurality of activity enhancers and the activity enhancers include L-theanine, thiamine, magnesium citrate, and zinc.

In one example, the formulation above further comprises magnesium stearate.

In one example, the at least one activity enhancer in the formulation comprises from about 1 wt % to about 75 wt % of the formulation.

In one example, the at least one activity enhancer in the formulation is in a form of a pharmaceutically acceptable salt.

In one example, the *Sceletium* extract in the formulation is present from about 3 wt % to about 15 wt % and the at least one activity enhancer is present in the formulation from about 1 wt % to about 75 wt %.

In one example, the formulation further comprises a pharmaceutically acceptable carrier.

In one example, the pharmaceutically acceptable carrier in the formulation comprises cellulose, gelatin, water or mixtures thereof.

In one example, the formulation further comprising at least one member selected from the group consisting of flavorings, preservatives, vitamins, or minerals.

In one example, the formulation is an oral dosage formulation.

In one example, the oral dosage form comprises a capsule, a tablet, a powder, a beverage, a syrup, a suspension, or a food.

In one example, the formulation comprises from about 0.1 mg to about 10,000 mg of the *Sceletium* extract.

In one example there is provided, a *Sceletium* extract dosage form for administration to a subject to inhibit phosphodiesterase type IV (PDE4) activity comprising:
  an amount of a *Sceletium* extract and an amount of at least one activity enhancer, wherein when administered to a subject, the dosage is more effective at inhibiting PDE4 than either the amount of *Sceletium* extract or the amount of the activity enhancer alone.

In one example, the amount of *Sceletium* extract in the dosage form is a therapeutically effective amount without the activity enhancer.

In one example, the amount of *Sceletium* extract in the dosage form is not a therapeutically effective amount without the activity enhancer.

In one example, the amount of the *Sceletium* extract in the dosage form is from about 0.01 mg to about 30,000 mg.

In one example, the amount of the *Sceletium* extract in the dosage form is from about 0.01 mg to about 10,000 mg.

In one example, the amount of the *Sceletium* extract in the dosage form is from about 0.1 mg to about 100 mg.

In one example, the amount of the at least one activity enhancer in the dosage form is from about 0.01 mg to about 10,000 mg.

In one example, the amount of the at least one activity enhancer in the dosage form is from about 1 mg to about 125 mg.

In one example, the *Sceletium* extract is present in the dosage form at an amount of from about 1 mg to about 100 mg and the at least one activity enhancer is present in an amount of from about 1 mg to about 125 mg.

In one example, the dosage form is prepared for administration to a subject according to a predetermined regimen.

In one example, the dosage form is administered in the regimen is a once per day administration.

In one example, the dosage form is administered according to a predetermined regimen that is a multiple time per day administration.

In one example, the dosage form is administered in an oral dosage form, a transdermal dosage form, a transmucosal dosage form, an inhalant dosage form, or a parenteral dosage form.

In one example there is provided, a method of inhibiting phosphodiesterase type IV (PDE4) activity in a subject comprising:
  administering an amount of a *Sceletium* extract and at least one activity enhancer to the subject.

In one example, the activity enhancer used in the method is a member selected from the group consisting of: L-theanine, thiamine, zinc gluconate, magnesium citrate, magnesium stearate, cellulose, or a mixture thereof.

In one example, in the method the PDE4 inhibiting effect is greater than an effect provided by either the amount of *Sceletium* extract or the amount of activity enhancer alone.

In one example, in the method the PDE4 inhibition provides treatment of signs or symptoms of a condition selected from the group consisting of: anxiety related disorders, depression related disorders, allergic disorders, autoimmune disorders, diabetes associated disorders, inflammatory conditions, neurological disorders, or cardiovascular diseases.

In one example, the method provides treatment for an anxiety related disorder.

In one example, the method provides treatment for a depression related disorder.

In one example, the method is administered to a subject that is a mammal.

In one example, the mammal is a human.

In one example, the mammal is a domesticated or farm animal.

In one example, the method of treatment is prophylactic.

In one example of the method, the *Sceletium* extract and at least one activity enhancer formulation are administered orally, rectally, ophthalmicly, nasally, nasally by inhalation, topically, vaginally, parentally, by implantation, or intramuscularly.

In one example, the *Sceletium* extract and at least one activity enhancer are administered orally.

In one example, the *Sceletium* extract and at least one activity enhancer are administered concurrently.

In one example, the *Sceletium* extract and at least one activity enhancer are administered from a single formulation.

In one example, the *Sceletium* extract and at least one activity enhancer are administered separately.

In one example, the *Sceletium* extract and the at least one activity enhancer are administered sequentially.

In one example there is provided, a method of increasing phosphodiesterase type IV (PDE4) inhibition activity of an amount of a *Sceletium* extract comprising:
  adding an amount of at least one activity enhancer, wherein the combination of *Sceletium* extract and the at least one activity enhancer inhibits PDE4 activity to a greater degree than the amount of *Sceletium* alone.

In one example, the PDE4 inhibition occurs in a subject to whom the *Sceletium* extract and the at least one activity enhancer are administered.

In one example, the *Sceletium* extract and the at least one activity enhancer is added to a formulation containing the *Sceletium* extract.

In one example, the at least one activity enhancer is added to the *Sceletium* extract upon administration of the activity enhancer to a subject.

In one example, the increase in PDE4 inhibition activity is more than an additive effect of administering the amount of *Sceletium* extract and the amount of at least one activity enhancer alone.

In one example, the increase in PDE4 inhibition activity is from about 30% to about 80% greater than that achieved by administering either the *Sceletium* extract or the activity enhancer alone.

In one example, the *Sceletium* extract is from at least one of *S. tortuosum, S. strictum, S. subvelutinum, S. joubertii,* and *S. namaquense*, or a combination thereof.

In one example, the *Sceletium* extract is from *S. tortuosum*.

In one example, the at least one activity enhancer is a member selected from the group consisting of: L-theanine, thiamine, zinc gluconate, magnesium citrate, magnesium stearate, cellulose, or mixtures thereof.

In one example, the at least one activity enhancer is L-theanine.

In one example, the at least one activity enhancer is thiamine.

In one example, the amount of at least one activity enhancer is added to the amount of *Sceletium* extract at a ratio of from about 1:1 to about 20:1.

In one example, the ratio is from about 2:1 to about 15:1

In one example, the ratio is about 14:1.

In one example of the method, the at least one enhancer is added in an amount of 345 mg to a formulation containing 25 mg of *Sceletium* extract.

In one example there is provided a phosphodiesterase type IV (PDE4) inhibiting system, comprising:
  an amount of a *Sceletium* extract; and
  an amount of at least one activity enhancer.

In one example, the *Sceletium* extract and the at least one activity enhancer are separate from one another.

In one example, the *Sceletium* extract and the at least one activity enhancer are in separate formulations.

In one example, the *Sceletium* extract and the at least one activity enhancer are in a single formulation.

In one example, the amount of *Sceletium* extract and the amount of at least one activity enhancer are more effective at inhibiting PDE4 together than either the amount of *Sceletium* extract or the amount of at least one activity enhancer alone.

In one example, the effect of the combined amount of *Sceletium* extract and the amount of at least one activity enhancer is more than additive.

In one example, the PDE4 inhibiting effect of the combined amount of *Sceletium* extract and the amount of at least one activity enhancer is from about 30% to about 80% greater than that achieved by administering the amount of *Sceletium* extract or the amount of activity enhancer alone.

In one example, the *Sceletium* extract is derived from at least one of *S. tortuosum, S. strictum, S. subvelutinum, S. joubertii,* and *S. namaquense* or a combination thereof.

In one example, the *Sceletium* extract is derived from *S. tortuosum*.

In one example, the amount of the amount of *Sceletium* extract is from about 0.01 mg to about 30,000 mg.

In one example, the amount of *Sceletium* extract is from about 0.01 mg to about 10,000 mg.

In one example, the amount of *Sceletium* extract is from about 1 mg to about 100 mg.

In one example, the amount of the at least one activity enhancer is from about 0.01 mg to about 10,000 mg.

In one example, the amount of the at least one activity enhancer is from about 1 mg to about 125 mg.

In one example, the *Sceletium* extract and the at least one activity enhancer are packaged together.

In one example, a method for modulating a diseases-related protein kinase activity in a subject comprising:
  administering to the subject a formulation having an amount of a *Sceletium* extract in combination with an amount of at least one activity enhancer, wherein when administered to a subject, the formulation is more effective at modulating the protein kinase activity then either the amount of *Sceletium* extract or the amount of activity enhancer alone.

In one example of the method, the disease-related protein kinase activity is selected from the group consisting of ABL, AKT, AURORA, CDK, DBF2/20, EGFR, EPH/ELK/ECK, ERK/MAPKFGFR, GSK3, IKKB, INSR, JAK DOM 1/2, MARK/PRKAA, MEK/STE7, MEKK/STE11, MLK, mTOR, PAK/STE20, PDGFR, PI3K, PKC, POLO, SRC, TEC/ATK, and ZAP/SYK.

In one example of the method, the disease related protein kinase activity is modulated in a protein kinase selected from the group consisting of CLK1, Met, Syk, Aurora, PRAK, Flt4, TrkC, CK2α2, MSSk1, Fms, and GSK3.

In one example of the method, the disease related protein kinase plays a functional role in an anxiety condition in the subject.

In one example there is provided a method of preparing a phosphodiesterase type IV (PDE4) activity inhibiting formulation, comprising:
  combining a *Sceletium* extract with at least one activity enhancer in a manner suitable for administration to a subject.

In one example, there is provided a composition for enhancing the PDE4-inhibitory activity of *Sceletium* in a subject comprising a therapeutically effective amount of at least one member selected from the following group comprising:
  a. from about 0.01 mg to about 10,000 mg of aerial parts of *Sceletium;*
  b. from about 0.01 mg to about 10,000 mg of an extract of *Sceletium tortuosum;*
  c. from about 0.01 mg to about 10,000 mg of a compound derived from *Sceletium;*
and at least one member from the following group comprising:
  d. from about 0.01 mg to about 10,000 mg of L-theanine;
  e. from about 0.01 mg to about 10,000 mg of thiamine;
  f. from about 0.01 mg to about 10,000 mg of zinc gluconate;
  g. from about 0.01 mg to about 10,000 mg of magnesium citrate;
  h. from about 0.01 mg to about 10,000 mg of magnesium stearate;
  i. from about 0.01 mg to about 10,000 mg of cellulose.

In one example, there is provided a method for enhancing the PDE4-inhibitory activity of *Sceletium* administered to a subject comprising administering a therapeutically effective amount of at least one member selected from the following group comprising:

a. from about 0.01 mg to about 10,000 mg of aerial parts of *Sceletium*;

b. from about 0.01 mg to about 10,000 mg of an extract of *Sceletium tortuosum*;

c. from about 0.01 mg to about 10,000 mg of a compound derived from *Sceletium*;

and at least one member from the following group comprising:

d. from about 0.01 mg to about 10,000 mg of L-theanine;

e. from about 0.01 mg to about 10,000 mg of thiamine;

f. from about 0.01 mg to about 10,000 mg of zinc gluconate;

g. from about 0.01 mg to about 10,000 mg of magnesium citrate;

h. from about 0.01 mg to about 10,000 mg of magnesium stearate;

i. from about 0.01 mg to about 10,000 mg of cellulose.

Thus, there have been disclosed novel compositions of *Sceletium* and/or *Sceletium* extract, such as *S. tortuosum* and methods of synergistically inhibiting PDE4. Methods for the production of these formulations and uses have been described. It will be readily apparent to those skilled in the art, however that various changes and modifications of an obvious nature may be made without departing from the spirit of the disclosed invention embodiments, and all such changes and modifications are considered to fall within the scope of the invention as recited herein, including in the appended claims. Examples of such changes and modifications could include, but not be limited to, the incipient ingredients added to affect the capsule, tablet, powder, lotion, food or bar manufacturing process as well as vitamins, flavorings and carriers. Other examples of such changes or modifications could include the use of herbs or other botanical products containing the combinations of the preferred embodiments disclosed above.

What is claimed is:

1. A phosphodiesterase type IV (PDE4) activity inhibiting formulation, comprising:

an *Sceletium* extract in combination with an effective amount of at least one activity enhancer, said activity enhancer comprising an amino acid, a metal, a vitamin, a polysaccharide, or combination thereof, wherein when administered to a subject, the formulation has synergistic effect at inhibiting PDE4 activity.

2. The formulation of claim 1, wherein the PDE4 inhibiting effect of the formulation on the subject is from about 30% to about 80% greater than that achieved by administering either the *Sceletium* extract or the activity enhancer alone.

3. The formulation of claim 1, wherein the *Sceletium* extract is from at least one of *S. tortuosum, S. strictum, S. subvelutinum, S. joubertii,* and *S. namaquense* or a combination thereof.

4. The formulation of claim 3, wherein the *Sceletium* extract is from *S. tortuosum*.

5. The formulation of claim 1, wherein the *Sceletium* extract comprises from about 1 wt % to about 50 wt % of the formulation.

6. The formulation of claim 1, wherein the activity enhancer has substantially no PDE4 inhibitory effect of its own.

7. The formulation of claim 1, wherein the activity enhancer is a member selected from the group consisting of: L-theanine, thiamine, zinc gluconate, magnesium citrate, magnesium stearate, cellulose, or a mixture thereof.

8. The formulation of claim 1, wherein the at least one activity enhancer comprises L-theanine.

9. The formulation of claim 1, wherein the at least one activity enhancer comprises thiamine.

10. The formulation of claim 1, wherein the at least one activity enhancer comprises from about 1 wt % to about 75 wt % of the formulation.

11. The formulation of claim 1, wherein the formulation further comprises a pharmaceutically acceptable carrier.

12. The formulation of claim 1, wherein the formulation is an oral dosage formulation.

13. The formulation of claim 12, wherein the oral dosage form comprises a capsule, a tablet, a powder, a beverage, a syrup, a suspension, or a food.

14. The formulation of claim 13, wherein the formulation comprises from about 0.1 mg to about 10,000 mg of the *Sceletium* extract.

* * * * *